US00PP27545P3

(12) United States Plant Patent
Warren

(10) Patent No.: US PP27,545 P3
(45) Date of Patent: Jan. 17, 2017

(54) MAPLE TREE NAMED 'JFS-KW187'

(50) Latin Name: *Acer truncatum*
Varietal Denomination: JFS-KW187

(71) Applicant: J. Frank Schmidt & Son Co., Boring, OR (US)

(72) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 125 days.

(21) Appl. No.: 14/545,226

(22) Filed: Apr. 8, 2015

(65) Prior Publication Data

US 2016/0302340 P1 Oct. 13, 2016

(51) Int. Cl.
*A01H 5/00* (2006.01)

(52) U.S. Cl.
USPC ..... Plt./224

(58) Field of Classification Search
USPC ..... Plt./216, 224
See application file for complete search history.

*Primary Examiner* — Susan McCormick Ewoldt
*Assistant Examiner* — Karen Redden
(74) *Attorney, Agent, or Firm* — Klarquist Sparkman, LLP

(57) ABSTRACT

A variety of maple tree which combines compact growth, dense branching, a narrow upright growth habit, glossy foliage, and bright fall color.

11 Drawing Sheets

Latin name of the genus and species of the plant claimed: *Acer truncatum.*

Variety denomination: 'JFS-KW187'.

BACKGROUND OF THE INVENTION

In 1983, I initiated a program of selection and improvement in the species *Acer truncatum*. I obtained seed and seedlings from several sources that were planted out for evaluation. As part of this program, in March of 1988, I selected four particularly nice seedlings which I planted into a trial block in a nursery in Boring, Oreg. After several years of evaluation, I determined that one of these trees, which I designated *Acer truncatum* 'D' (unpatented) was the best in terms of foliage quality, form, and fall color. I allowed 'D' to develop seed from open pollination in the block with many other selected seedlings of *Acer truncatum*. In October of 1992, I collected this seed from *Acer truncatum* 'D' and grew them in a seedbed in Boring, Oreg. From this seed, I obtained 58 seedlings which I planted out into a nursery row in Boring, Oreg. in April of 1994. From these 58 seedlings, I selected the best eight to be saved and transplanted in 1997 for further evaluation. The remaining seedlings of this group of 58 seedlings were destroyed. Several years after picking the seed, the parent tree *Acer truncatum* 'D' was destroyed when the block was cleared due to crowding and my evaluations had determined that the selected seedling trees were superior to the seed parent 'D'.

Of the eight selected seedlings that were transplanted in 1997, I selected the best single tree in August of 1998 which I designated as *Acer truncatum* 'JFS-KW187'. My attention was first drawn to 'JFS-KW187' because of its very dense, compact, form and its strongly upright growth habit. I later discovered that this 'JFS-KW187' tree had superior fall color. In August 1998, I began asexual propagation trials by budding from the original 'JFS-KW187' tree onto *Acer platanoides* rootstock. From this vegetative propagation, I obtained six trees which I compared to the original 'JFS-KW187' tree. Subsequently, I vegetatively propagated additional small trial plots of six to twelve 'JFS-KW187' trees in 2004, 2007, 2008, and 2009. All of these trial trees were destroyed after evaluation except for one 'JFS-KW187' tree that was planted into a long term trial block in 2011 in Boring, Oreg., and eight other 'JFS-KW187' trees that were saved to become a future propagation source in a stock block in a nursery in Canby, Oreg. in 2013. My original tree of 'JFS-KW187' was moved to a long term trial block in Boring, Oreg. in February, 2002.

This asexual propagation in Boring, Oreg. by budding on *Acer platanoides* rootstock has shown that the characteristics of my new tree are firmly fixed in successive generations. Testing, evaluation, and comparison of *Acer truncatum* 'JFS-KW187' trees has convinced me that my new tree has superior form and appearance for landscape use.

SUMMARY OF THE INVENTION

This new cultivar possesses a unique combination of characteristics in that it combines compact growth, dense branching, a narrow upright growth habit, glossy foliage, and bright fall color.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
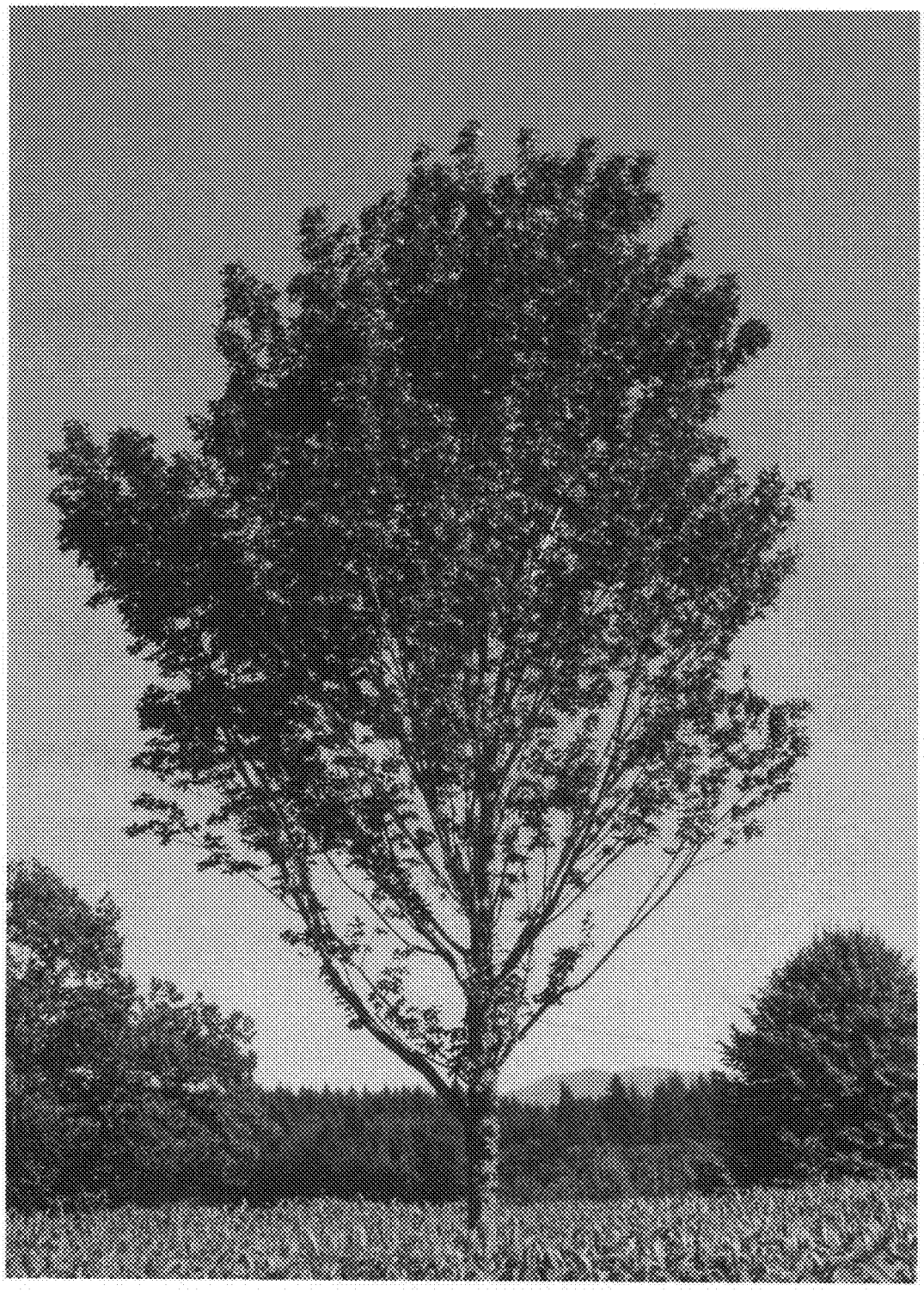
FIG. 1: Shows the original 'JFS-KW187' tree at 21 years of age in summer foliage illustrating its upright growth habit and color of foliage.
Figure 2:
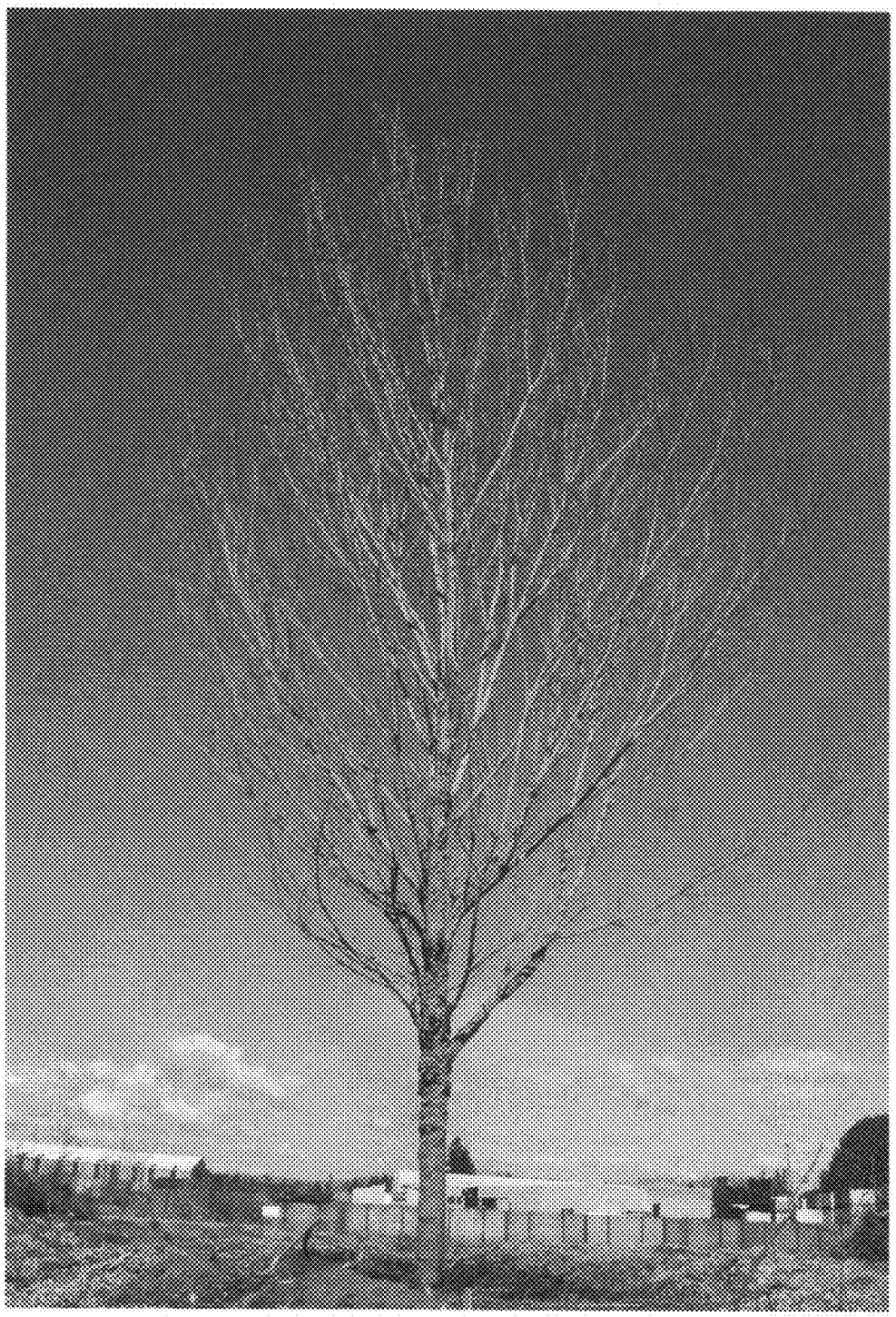
FIG. 2: Shows the original 'JFS-KW187' tree at 21 years of age during the winter dormant season illustrating the density of its branching, its straightness, and the stiffly ascending orientation of its branches.
Figure 3:
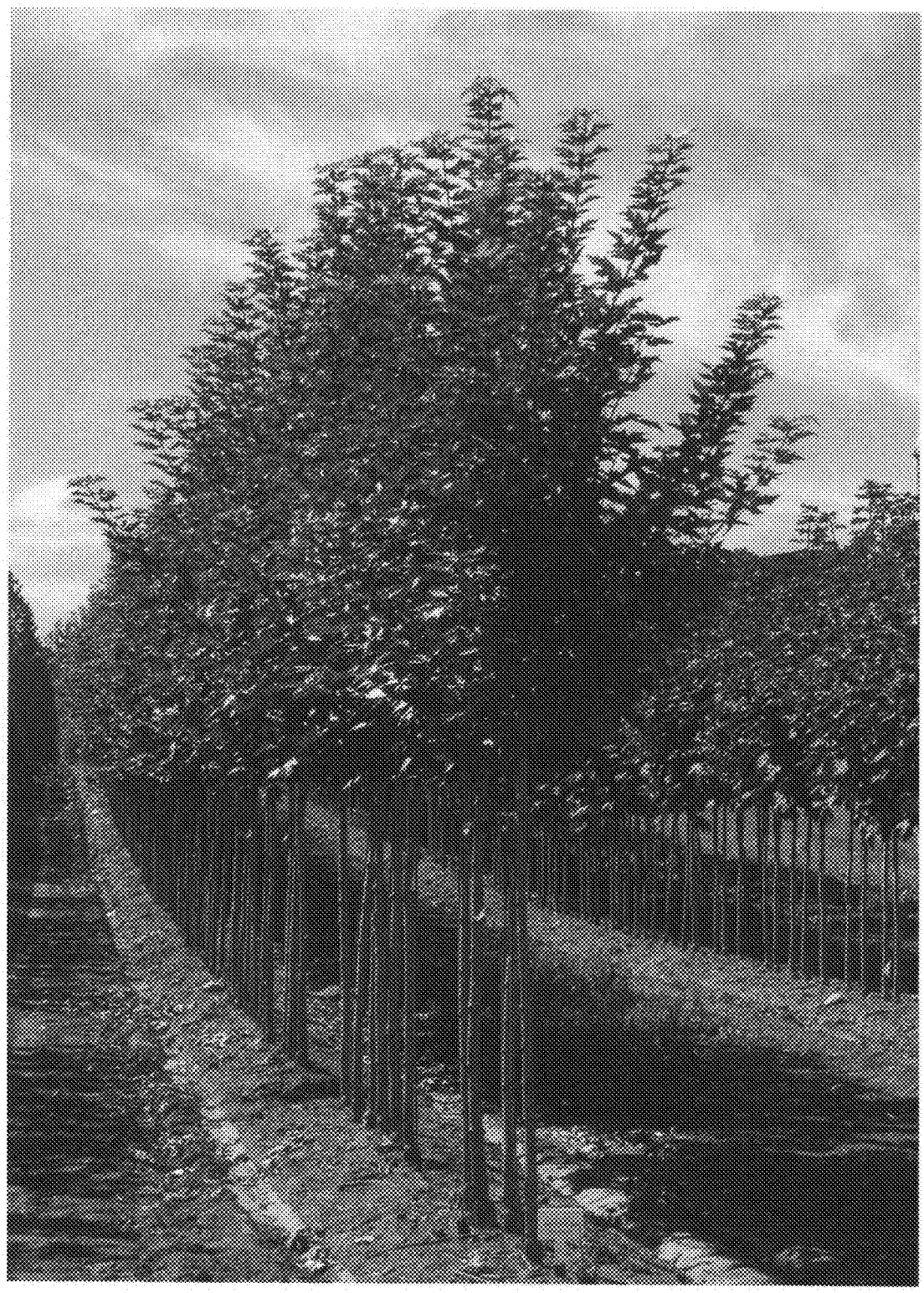
FIG. 3: Shows 2 year old vegetatively propagated 'JFS-KW187' trees in a nursery row in summer foliage showing the upward growth habit and stiffly ascending branch orientation at this age.
Figure 4:
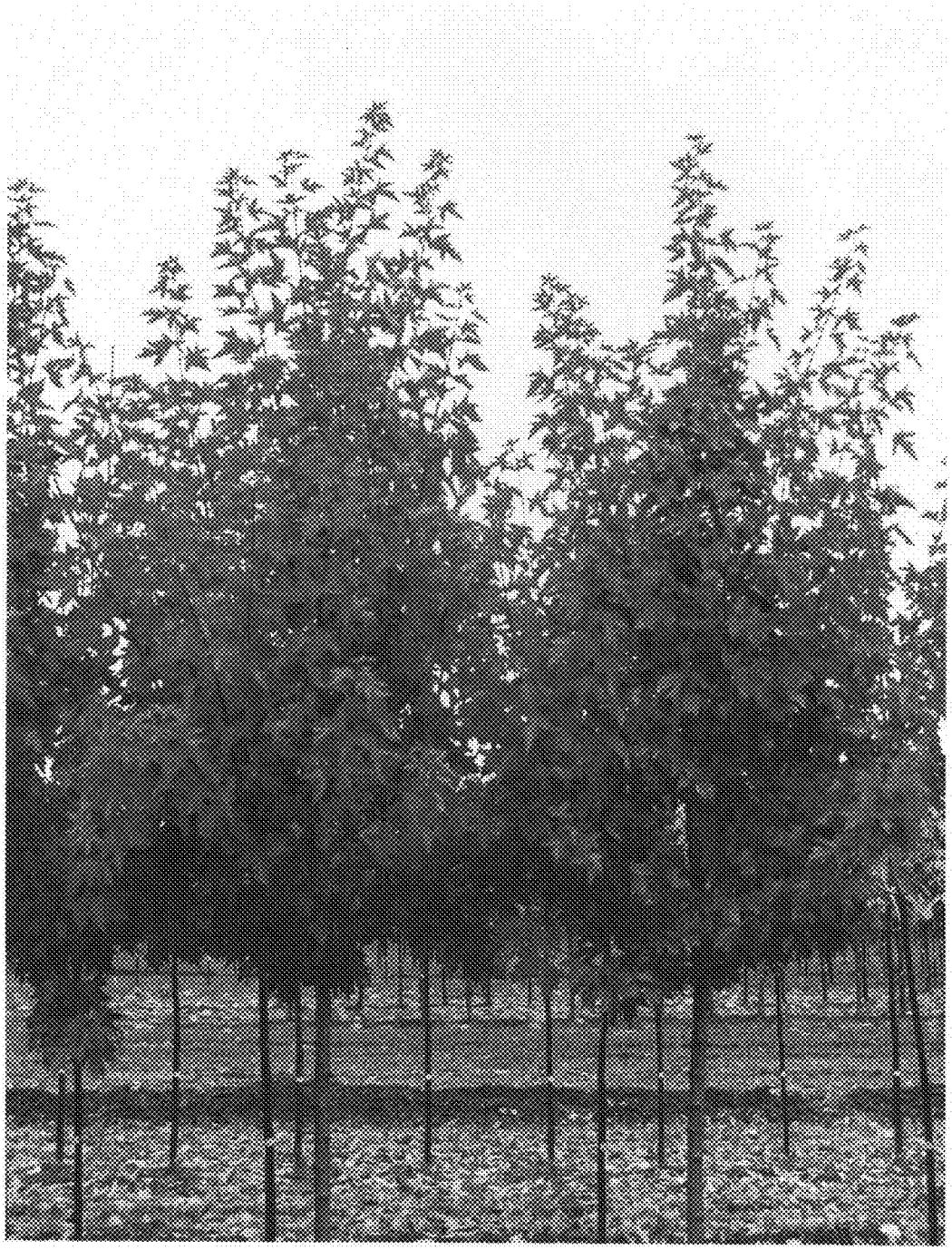
FIG. 4: Shows 3 year old vegetatively propagated 'JFS-KW187' trees in a nursery row in fall foliage showing the density of branching, the upward growth habit, and stiffly ascending branch orientation at this age.
Figure 5:
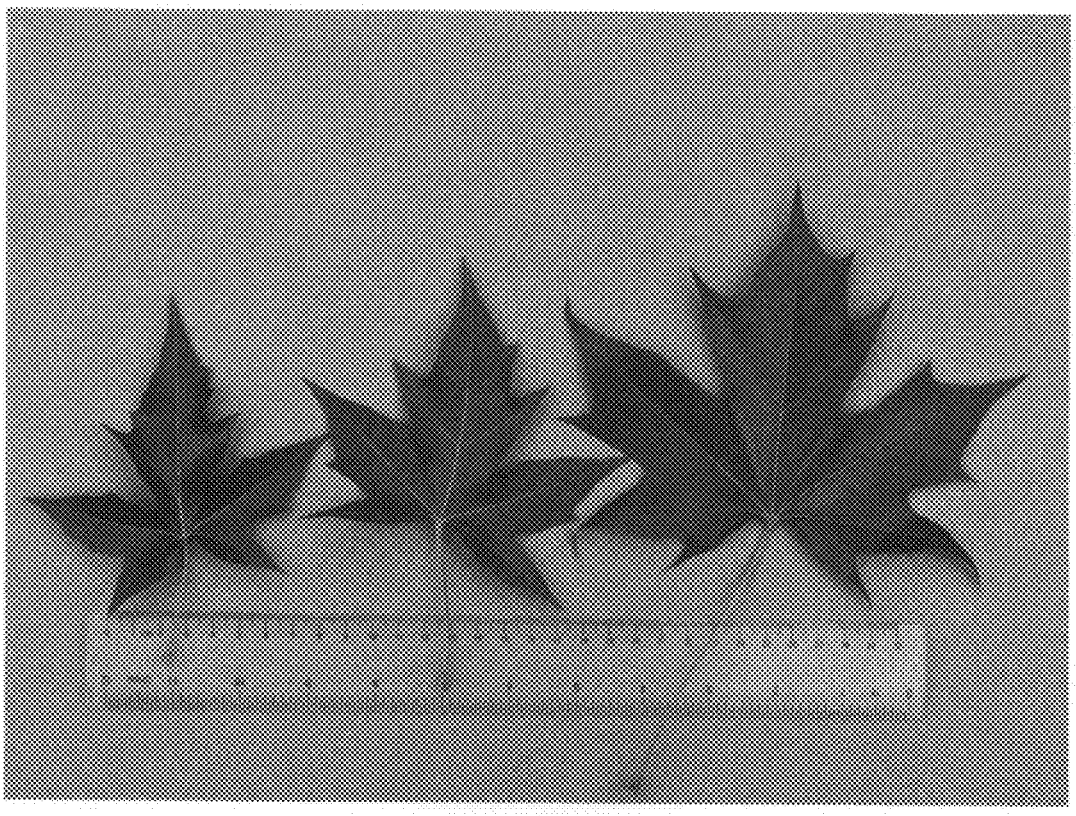
FIG. 5: Shows the upper surface of leaves from a 'JFS-KW187' tree in summer illustrating the color and shape.
Figure 6:
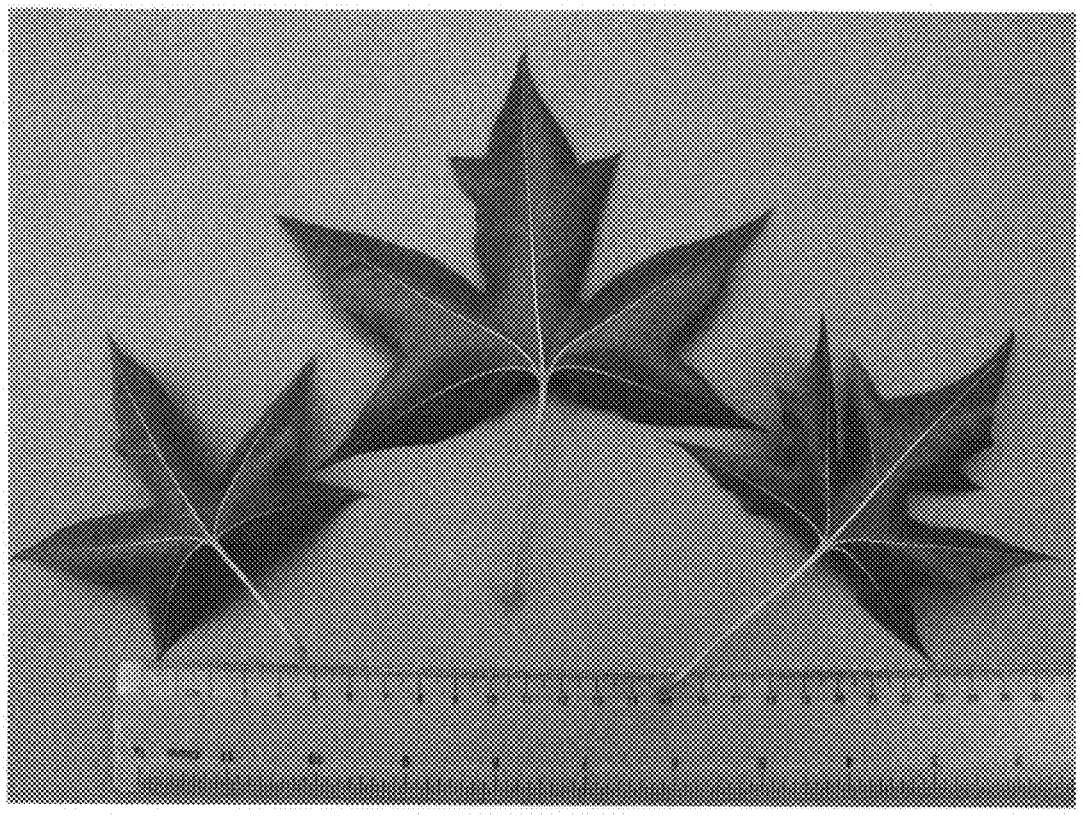
FIG. 6: Shows the lower surface of leaves from a 'JFS-KW187' tree in summer illustrating the color, the shape, and the prominent palmate veins.
Figure 7:
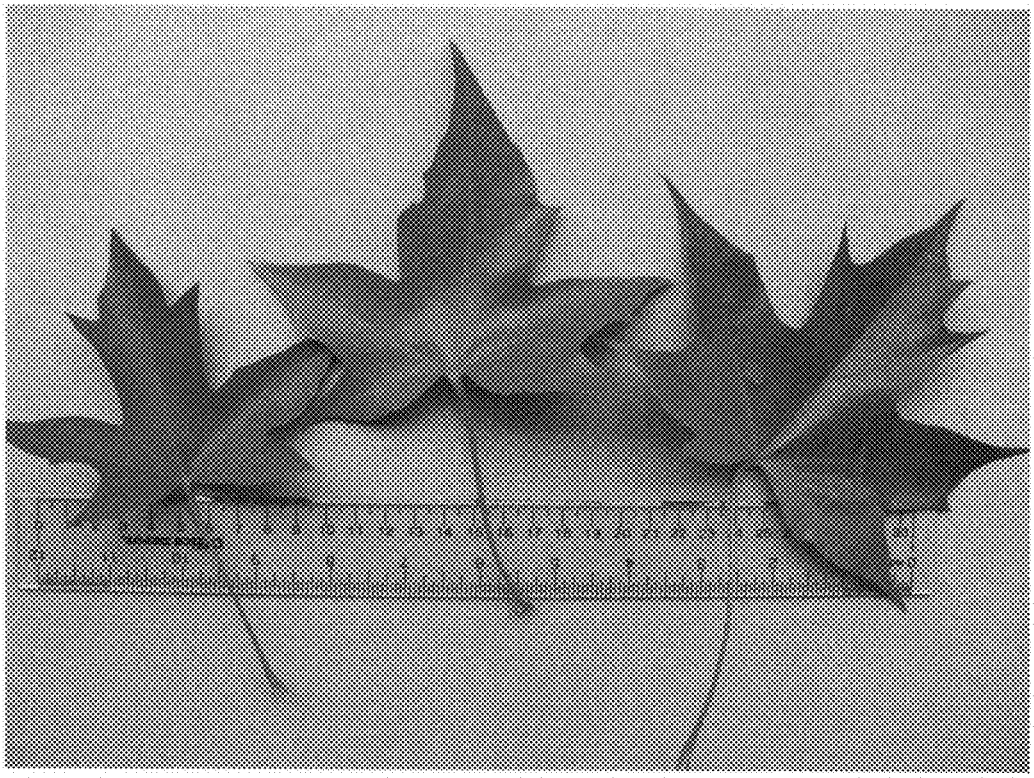
FIG. 7: Shows the upper surface of leaves from a 'JFS-KW187' tree in autumn illustrating the fall color.
Figure 8:
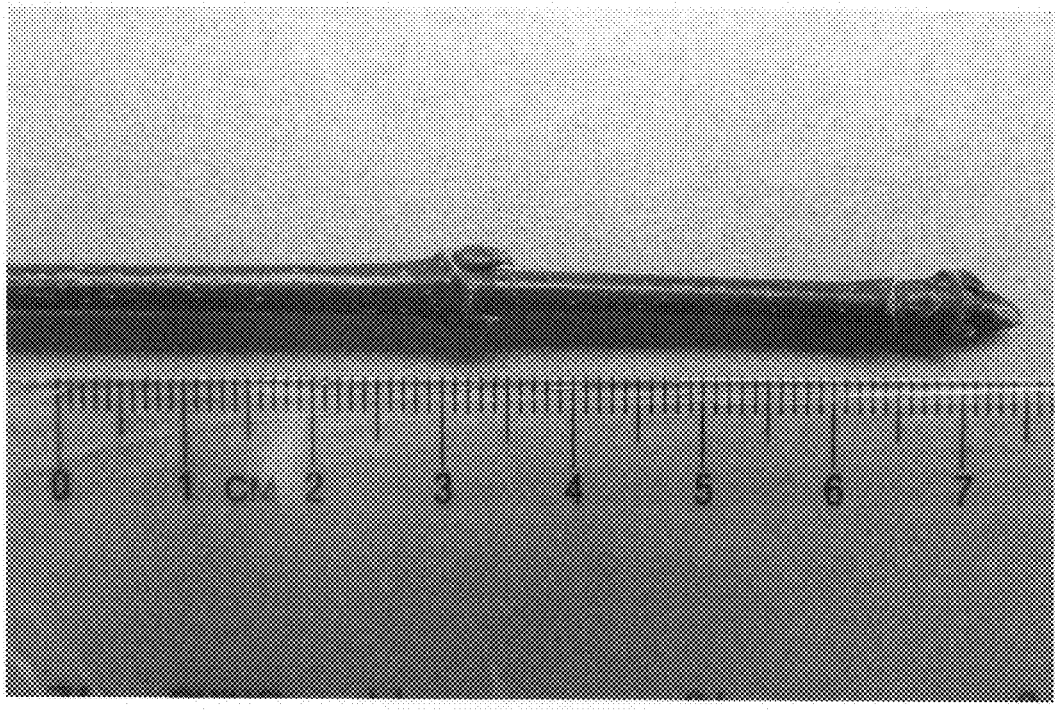
FIG. 8: Shows the dormant buds of a 'JFS-KW187' tree during winter.
Figure 9:
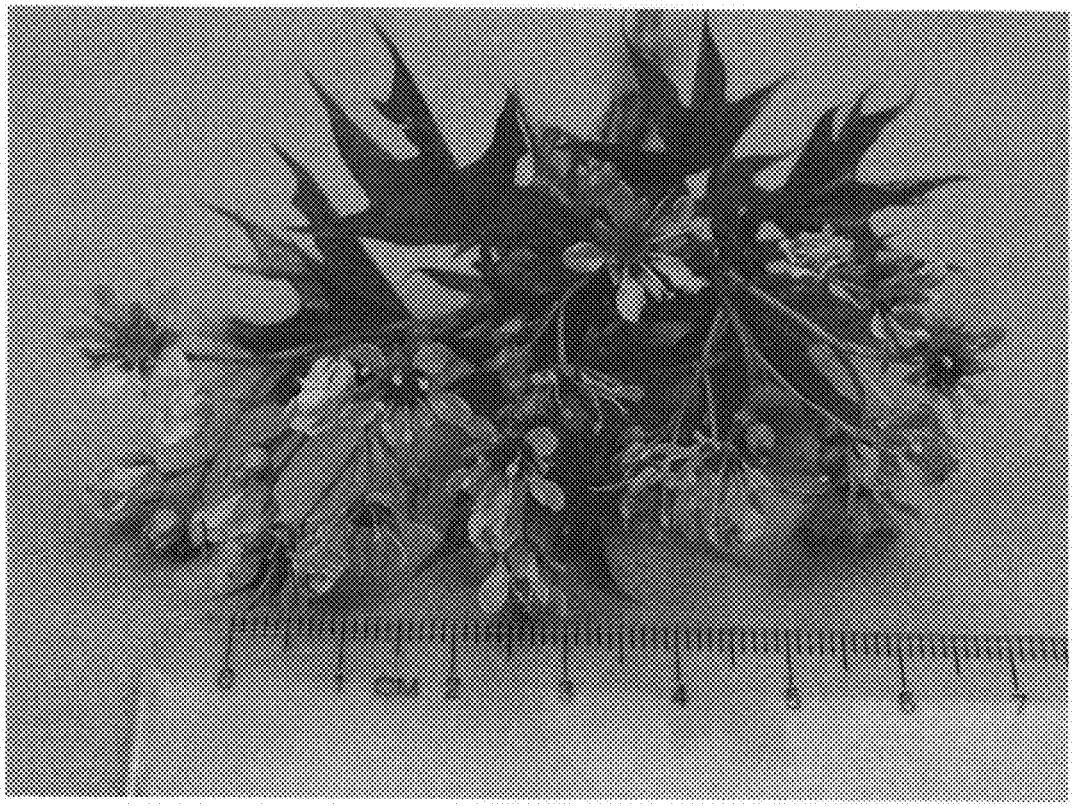
FIG. 9: Shows a corymb of male flowers of a 'JFS-KW187' tree in early spring illustrating that all flowers in male corymbs are male.
Figure 10:
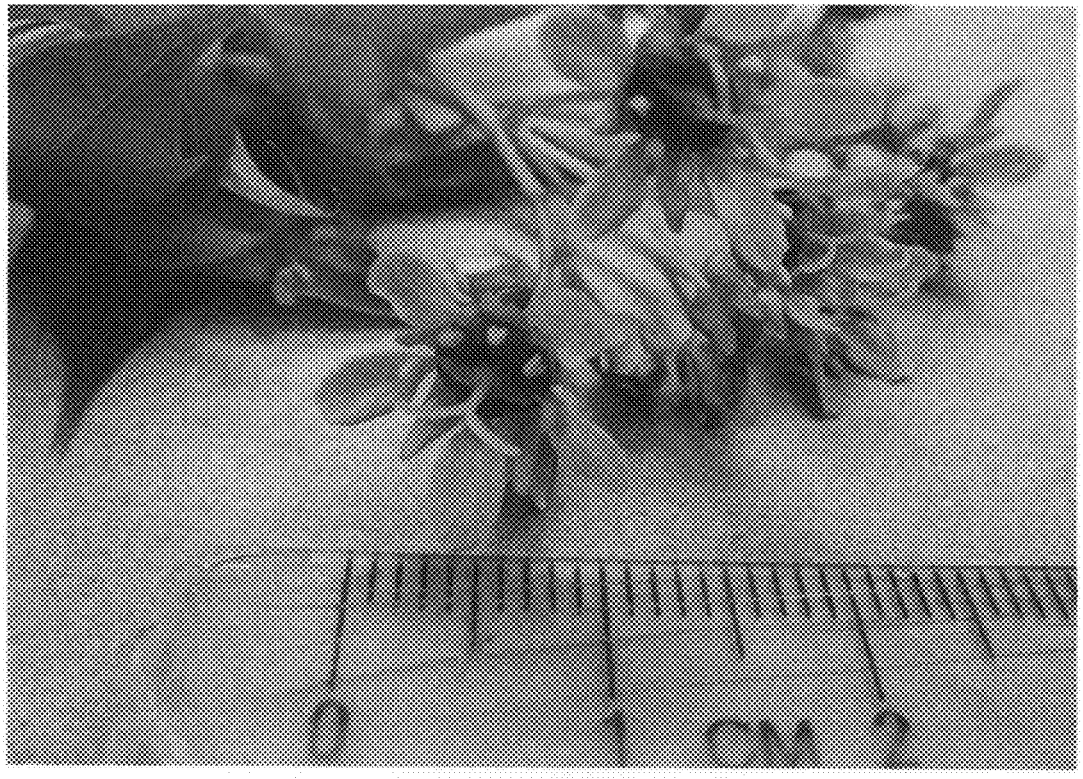
FIG. 10: Shows a close up of a female flower of a 'JFS-KW187' tree in a female corymb in spring illustrating the pistil with its two part style and the ovary with two carpels.
Figure 11:
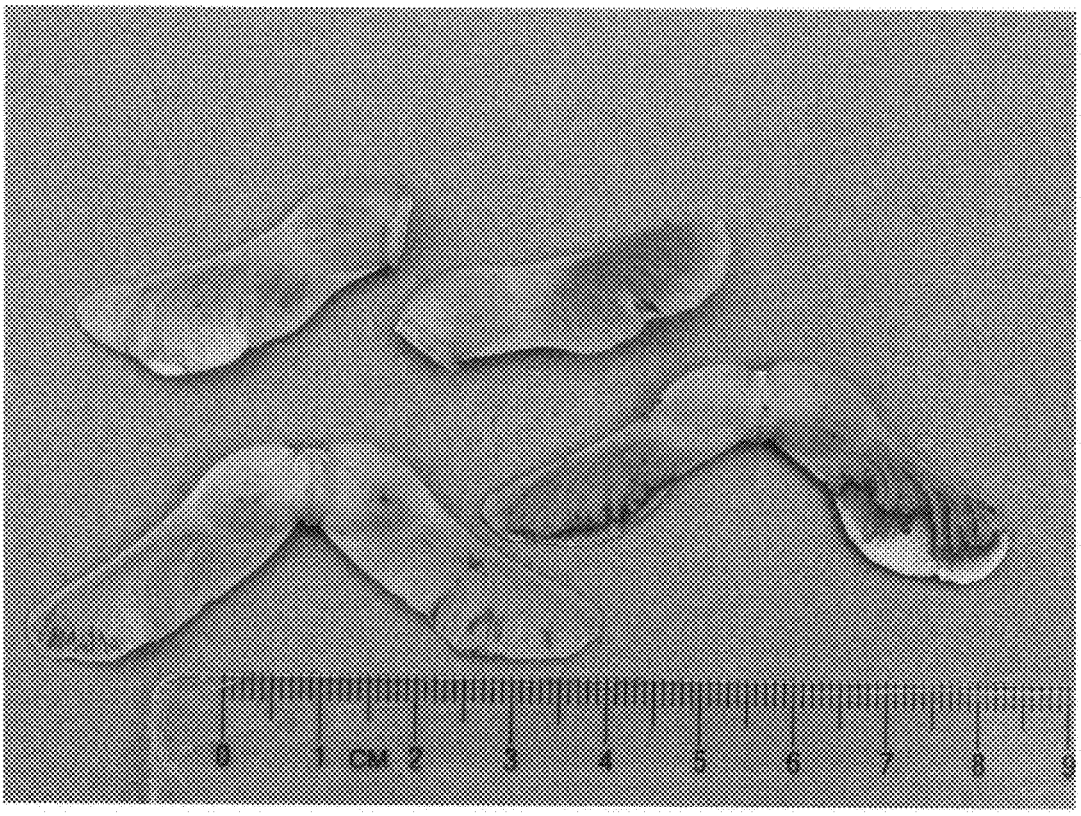
FIG. 11: Shows the samaras from a 'JFS-KW187' tree in autumn as they are ripening to maturity.

The following detailed description of the 'JFS-KW187' variety is based on observations of the original 'JFS-KW187' tree and one, two, and three year old vegetatively propagated 'JFS-KW187' progeny. The observed 'JFS-KW187' progeny were trees which were growing in Boring, Oreg. Color descriptions found below use terminology in accordance with The Royal Horticultural Society (London) Colour Chart© 1986, except where ordinary dictionary significance of color is indicated.

Scientific name: *Acer truncatum* 'JFS-KW187'.

Parentage:

*Seed parent*.—A selected seedling of *Acer truncatum* that I designated as *Acer truncatum* 'D', not patented, never commercially introduced, and since destroyed.

*Pollen parent*.—Unknown.

Tree:

*Overall shape*.—Pyramidal.

*Height*.—9.7 meters at 21 years of age.

*Width*.—5.5 meters at 21 years of age.

*Caliper*.—25.5 cm at 10 cm height above ground and 21.8 cm at 1 meter above ground at 21 years of age.

*Trunk*.—Stout, straight.

*Trunk bark texture*.—Slightly rough, vertically fissured.

*Trunk bark color*.—Immature bark color: Grey-brown 199A to Greyed-brown 197A. Mature bark color: Greyed-green 197A to Greyed-green 197C on ridges of bark and Grey-brown 199C to Grey-brown 199D in fissures.

*Lenticels*.—Not visible on mature trunk.

*Primary branches*.—Stiffly ascending at 35° to 45° from vertical.

*Branch color*.—Greyed-green 197B to Greyed-green 198A.

*Branch lenticels*.—Round, 1 mm in diameter on younger branches then disappearing into the bark by the fifth year. Orange-white 159B to Greyed-yellow 161D.

*Dormant buds*.—Ovoid, slightly adpressed against the twig, 2 mm to 5 mm long by 2 mm to 3 mm wide by 1 mm to 2 mm thick, with overlapping scales. Greyed-orange 177A to Greyed-purple 183A.

*Bud break*.—Bud break averages March 20 in Boring, Oreg.

*Internodes*.—Average length 7.1 cm when measured at the mid-point of a 1 year old tree.

*Hardiness*.—Has tolerated field temperatures to 5 degrees F. without damage in Boring, Oreg. This is the minimum temperature this location experienced during the life of the tree. It is believed to have Zone 5 cold hardiness similar to other plants of this species.

*Disease resistance*.—It has shown moderately good resistance to powdery mildew.

Leaves: Except as otherwise noted, observations are from twenty vigorous growth leaves.

*Arrangement*.—Opposite.

*Type*.—Simple.

*Texture*.—Smooth.

*Sheen*.—Very glossy.

*Length*.—10 cm to 14 cm, averaging 11.4 cm on leaves from 2 year old nursery trees.

*Width*.—12 cm to 21 cm, averaging 14.6 cm on leaves from 2 year old nursery trees.

*Petioles*.—6 cm to 9 cm long, averaging 7.3 cm on leaves from 2 year old nursery trees. Diameter 1.5 mm to 2.0 mm.

*Overall shape*.—Palmate with five major lobes.

*Margin*.—Entire.

*Tip*.—Acuminate.

*Base*.—Truncate to slightly sagittate.

*Stipules*.—None.

*Spring leaf color*.—First emerging leaves Yellow-green 151A to Yellow-green 144B with a tint of Greyed-purple 183 along the margin near the tip.

*Summer leaf color*.—Upper leaf surface: Green 139A to Yellow-green 147A. Lower leaf surface: Yellow-green 146A. Vein: Yellow-green 146A when shaded and varying to Greyed-red 178A where most exposed to sunlight. The vein is prominent on the undersurface of the leaf.

*Fall leaf color*.—Varies from Red 44A to Greyed-red 179A to Greyed-red 178A.

*Timing of fall leaf color*.—Average dates for original 'JFS-KW187' tree in Boring, Oreg. Onset: Averages October 21. Peak: Averages October 28. Latest extent of red fall color: Averages November 4. Fall color begins and peaks at a time that is typical for the species.

*Defoliation*.—Complete defoliation averages November 5 in Boring, Oreg.

*Pubescence*.—None.

*Persistence*.—The tree is deciduous.

Flowers: Monoecious, with male and female flowers occurring in separate clusters on the tree. Observations of the original tree and its vegetatively propagated progeny show that the majority of flowers are male and that female flowers are quite infrequent. This parallels the observation that 'JFS-KW187' has produced only sparse seeds. Staminate flowers occur in corymbs of typically 30 to 60 flowers. The corymb is rounded, 6 to 8 cm in diameter. Flowers have 10 exerted stamens, Yellow-green 151B. Anthers are yellow 11A. Five petals are present, long oval to long obovate, each 2 mm wide by 5 mm long. Five sepals are present, acute, each 1.5 mm wide by 4 mm long. Pistillate flowers occur in corymbs of typically 15 to 30 flowers. The corymb is rounded, 5 to 6 cm in diameter. Flowers have 10 short, 2 mm long, vestigial, non-functioning stamens. The pistil is exerted, 3 mm to 4 mm long, and divides into a two parted style. The ovary is superior with two carpels. Female flowers are 10 mm to 13 mm in diameter with 5 petals and 5 sepals. Petals are long oval to long obovate, 2 mm wide by 5 mm long, Yellow 10A. Sepals are acute, 1.5 mm by 4 mm long, Yellow-green 151C. The pistil is Yellow-green 151B. Flowering begins about one week after vegetative bud break and continues for about two weeks, depending on weather conditions.

Fruit: Samaras are sparsely produced, less than the species. Samaras, held in pairs at angle of 100° to 120°, maturing in mid to late October in Boring, Oreg. Samara pairs typically occur in clusters of two to four. Individual samaras measure 30 to 40 mm long by 10 to 12 mm wide and 3 to 4 mm thick at the seed end becoming paper thin along the wing margin. Samara color varies with maturity: Green 153A to Yellow-green 150C when immature and tinted Red 182A when exposed to full sun, then with maturity and drying they become Greyed-yellow 161C.

COMPARISON TO OTHER CULTIVATED VARIETIES

My new variety is easily distinguished from the most similar cultivars by its growth rate as evidenced by its height, internode length, number of branches, and leaf color. The following table shows these differences as measured on one year old trees of my new 'JFS-KW187' variety and three comparison varieties growing in Boring, Oreg. My new variety is shorter, more densely branched, and more compact as evidenced by its lesser height, greater number of branches, and shorter internode length. In addition, the upper leaf surface differs in color.

Table 1 defines these differences.

TABLE 1

| Feature: | 'JFS-KW187' | 'JFS-KW202' PP 21,838 | 'Warrenred' PP 7,433 | 'Keithsform' PP 7,529 |
|---|---|---|---|---|
| Tree height | 188 cm | 236 cm | 320 cm | 308 cm |
| Internode length | 7.1 cm | 11.1 cm | 9.5 cm | 9.7 cm |
| Branches | 13.2 | 0.5 | 7.5 | 1.2 |
| Leaf color, top | Green 139A to Yellow-green 147A | Greyed-purple 187A | Yellow-green 146A to Green 137A and Green 137B | Yellow-green 147B to Green 137A |

COMPARISON TO THE SPECIES

My new tree differs from *Acer truncatum* in that it is more robust in growth and size, as evidenced by its larger leaves and longer internode length. Additionally, its leaf color differs. Differences are shown in Table 2, below.

TABLE 2

| Feature | JFS-KW187 | *Acer truncatum* |
|---|---|---|
| Leaf width | 14.6 cm | 9.0 cm |
| Leaf length | 11.4 cm | 9.8 cm |
| Leaf color, summer upper surface | Green 139A to Yellow-green 147A | Yellow-green 144A to 147A |
| Internode length | 7.1 cm | 4.1 cm |

I claim:

1. A new and distinct variety of maple tree, substantially as herein illustrated and described.

* * * * *